United States Patent [19]

Yamada et al.

[11] Patent Number: 5,258,305

[45] Date of Patent: Nov. 2, 1993

[54] **MANUFACTURE OF OPTICALLY ACTIVE 2-PHENYLPROPIONIC ACID AND 2-PHENYLPROPIONAMIDE FROM THE NITRILE USING *RHODOCOCCUS EQUI***

[75] Inventors: Hideaki Yamada; Toru Nagasawa, both of Kyoto, Japan

[73] Assignees: Nitto Chemical Industry Co., Ltd.; Lonza Japan, Ltd.; Hideaki Yamada, all of Japan

[21] Appl. No.: 849,768

[22] Filed: Mar. 12, 1992

[51] Int. Cl.$^5$ .................... C12P 13/02; C12P 7/40; C12P 41/00

[52] U.S. Cl. .................... 435/280; 435/129; 435/136; 435/843

[58] Field of Search .................... 435/280, 136, 129

[56] References Cited

U.S. PATENT DOCUMENTS 5,034,329 7/1991 Cerbelaud et al. ............... 435/280
5,089,405 2/1992 Cerbelaud et al. ............... 435/136

FOREIGN PATENT DOCUMENTS 344044 11/1989 European Pat. Off. .
348901  1/1990 European Pat. Off. .
433117  6/1991 European Pat. Off. .
920106  1/1992 World Int. Prop. O. .

OTHER PUBLICATIONS

Yamamoto K, Appl. Environ. Micro. 56:3125-29 (1990).
ATCC Catalog pp. 64, 184-188 (1989).
Gilligan et al., 1991, Production of R(−) and S(+)-2-Phenylpropionic Acid Using Nitrile Hydrolyzing Bacteria, Abstract No. 3G2p1, Nippon Nogeikagaku Kai 1991 Mar. 3, 1965-Japan Society for Bioscience, Biotechnology and Agrochemistry and copy of slides and verbal presentation.

*Primary Examiner*—Douglas W. Robinson
*Assistant Examiner*—S. Saucier
*Attorney, Agent, or Firm*—Pennie & Edmonds

[57] ABSTRACT

The present invention provides a method of obtaining optically active 2-phenylpropionic acid and 2-phenylpropionamide such as S-(+)-2-phenylpropionic acid, R-(−)-2-phenylpropionamide, and R-(−)-2-phenylpropionic acid from S-2-phenylpropionitrile or R,S-2-phenylpropionamide using a bacterium belonging to *Rhodococcus equi*.

Optically active 2-phenylpropionic acid and 2-phenylpropionamide are recovered in high yield and in quantities according to the method of the invention.

2 Claims, No Drawings

MANUFACTURE OF OPTICALLY ACTIVE 2-PHENYLPROPIONIC ACID AND 2-PHENYLPROPIONAMIDE FROM THE NITRILE USING RHODOCOCCUS EQUI

DETAILED DESCRIPTION OF THE INVENTION

Applicable Field in Industry

The present invention relates to the process for producing optically active 2-phenylpropionic acid and 2-phenylpropionamide. These compounds are important as material for various medicinal preparations and agrochemicals. Particularly, S-(+)-2-phenylpropionic acid is important in industry as a material of non-steroid anti-inflammatory agents.

PRIOR ARTS AND THEIR PROBLEMS

For production of optically active 2-phenylpropionic acid utilizing the action of micro-organisms, there have been known a number of procedures: one is to convert α-substituted nitrile or α-substituted amide both being racemic compounds to optically active α-substituted organic acids through the biological actions of micro-organisms belonging to Alcaligenes, Pseudomonas, Rhodopseudomonas, Corynebacterium, Acinetobacter, Bacillus Mycobacterium Rhodococcus or Candida. (see EP Publication No. 0348901), and a second constitutes a part of the procedure wherein optically active 2-substituted carboxylic acid is produced by contacting a racemic 2-substituted nitrile with micro-organisms belonging to Pseudomonas, Fusarium, Rhodococcus, Brevibacterium, Micrococcus, Bacteridium or Bacillus (see Japanese Patent Application KOKAI No. 257893/1990).

In the former method, however, with any micro-organism cited, its activity is low in producing optically active phenylpropionic acid, and in the latter method no concrete data have been given as to its production of optically active phenylpropionic acid, so that the characteristics of the optically active phenylpropionic acid produced and the biological activity of the micro-organisms used remain unknown.

MEANS BY WHICH TO SOLVE THE PROBLEMS

Under such situations the present inventors have made strenuous efforts for developing the method allowing an effective production of optically active phenylpropionic acid, and found that utilization of micro-organisms belonging to *Rhodococcus equi* enable production of S-(+)-phenylpropionic acid from R, S-2-phenylpropionitrile or R,S-2-phenylpropionamide with high recovery and concentration, and high optical purity, thus achieving the present invention. Namely, the present invention consists of: (1) a production of optically active 2-phenylpropionic acid by converting R, S-2-phenylpropionitrile or R, S-2-phenylpropionamide into S-(+)-2-phenylpropionic acid by means of the enzymatic actions derived from micro-organisms belonging to *Rhodococcus equi*; (2) production of optically active 2-phenylpropionamide by recovering the remaining R-(−)-2-phenylpropionamide, and (3) a production of optically active 2-phenylpropionic acid by hydrolyzing R-(−)-2-phenylpropionamide as obtained in (2) to R-(−)-2-phenylpropionic acid.

The micro-organisms used in the present invention should belong to *Rhodococcus equi*, or more specifically, *Rhodococcus equi* TG328 (bacterial strain No. FERM BP-3791) may be used. This micro-organism was newly isolated from soil by the present inventors and was designated as *Phodococcus equi* TG328 and was deposited with Fermentation Research Institute (FRI), Agency of Industrial Science and Technology, Ministry of International Trade and Industry of 1-3, Higashi 1-chome, Tsukuba-shi, Ibaraki-ken, 305 Japan and was assigned the accession number FERM BP-3791. The bacteriological characteristics of this organism are as follows.

BACTERIOLOGICAL PROPERTIES

(a) Morphology (1) Shape and size of the cell: $0.9-1.0\mu \times 3-10\mu$
(2) Presence or absence of cellular polymorphism: the cell has a long rod-like appearance at the initial phase of cultivation, develops into club-like form with snappings thereupon, and is divided into fragments each having a short rod-shaped appearance.
(3) Motility: none
(4) Spore: none
(5) Gram-stain: positive
(6) Acid fastness: negative
(7) Metachromatic bodies: observed

(b) Growth on Culture Media (at 30° C.)

(1) Cultivation on broth agar plates: colony of 1 mm in diameter (48 hours), round, smooth, flat, opaque and lightly orange in color.
(2) Cultivation on inclined broth agar plates: thread-like innocula having smooth surface, with the cross-section being slightly raised, suggesting its dryness, and pink in color.
(3) Cultivation on liquid media containing bouillon: innocula grow heavily while forming a bacterial membrane, and cause, in the course of growth, moderate turbidity leasing to precipitation.
(4) Cultivation by needle insertion into gelatin with buillon: innocula grow well at the surface, into a funnel-like form at the space along the needle insertion, and scarcely grow at the deepest part of the bore. Gelation does not undergo liquefaction.
(5) Lithmus milk,: no change is observed.

(c) Physiological Properties (1) Nitrate Reduction: Positive
(2) Denitrification reaction: negative
(3) MR test: negative
(4) VP test: negative
(5) Production of indoles: positive
(6) Production of hydrogen sulfide: positive
(7) Hydrolysis of starch: negative
(8) Utilization of citric acid
on Cauther's medium: negative
on Christensen's medium: negative
(9) Utilization of inorganic nitrogen sources
nitrates: positive
ammonium salts: positive
(10) Production of pigments: negative
(11) Urease: positive
(12) Oxidase: negative
(13) Catalase: Positive
(14) Hydrolysis of cellulose: negative
(15) Viable range
pH: 5-10
Temperature: 10°-41° C.

(16) Attitude to oxygen: aerobic
(17) Decomposition of tyrosine: negative
(18) Decomposition of adenine: positive
(19) Phosphatase: positive
(20) Hydrolysis of Tween 80: positive
(21) Thermal resistance
Measured in 10% skim milk at 72° C. for 15 min: none
(22) O-F test: O (strong)
(23) Production or acids and gases from sugars

|  | Acid production | Gas production |
| --- | --- | --- |
| L-araginose | − | − |
| D-xylose | − | − |
| D-glucose | + | − |
| D-mannose | − | − |
| D-fructose | + | − |
| Maltose | + | − |
| Sucrose | + | − |
| Lactose | − | − |
| Trehalose | + | − |
| D-sorbitol | + | − |
| D-mannitol | + | − |
| Glycerin | − | − |

(24) Growth on single carbon sources

| | |
| --- | --- |
| Inositol | − |
| Malose | − |
| D-mannitol | − |
| Rhamnose | − |
| D-sorbitol | − |
| m-hydroxybenzoic acid | (+) |
| sodium adipate | − |
| sodium benzoate | − |
| sodium citrate | − |
| sodium lactate | + |
| Testosterone | (+) |
| L-tyrosine | − |
| Glycerol (1%) (w/v) | (+) |
| Trehalose | (+) |
| p-hydroxybanzoic acid benzoic acid (1%) (w/v) | (+) |

(+) Indicates the action, though weak, being positive.

(25) Fatty acids and cell analysis: the cell contains saturated and unsaturatd straight fatty acids, and tuberculostearic acid. TLC of mycolic acid gives a single spot.

When strain TG328 is classified by the Bergey's Manual of Systematic Bacteriology (1986) according to the bacteriological properties described above, the bacterium has the following features: bacilliform, no endospore formation, aerobic, gram-positive, weakly acid-fast, catalase positive, and no flagellum. At the initial growth phase, the bacterium has a long rod-like appearance resembling filamentous mycelia, and in the following phase, it grows with branching, and the branch breaks later to form short bacillary fragments, resulting a shape to be classified to Nocardia type bacteria.

Analysis of fatty acid composition of the bacterium reveals that it contains saturated and unsaturated straight fatty acids containing tuberculostearic acid. Since TLC of mycolic acid gives a single spot whose Rf is the same as in *Rhodococcus equi* ATCC 6939, it can be distinguished from Mycobacterium. Further, because of the composition (number of carbons) of the mycolic acid, the bacterium be distinguished from Nocardia. From a study on its biochemical properties, it was concluded that this bacterium belongs to *Rhodococcus equi*.

Conversion of nitrile into acid utilizing microbial actions has been achieved through two reaction processes: one utilizing an enzyme nitrilase that produces directly the acid, and the other utilizing nitrile hydratase and amidase that produce the acid from amide. Said strain TG328 can produce through cultivation, nitrile hydratase and amidase simultaneously, and thus can work according to the latter reaction process, In the present invention, amidase produced in this reaction has a capacity of converting racemic R, S-2-phenylpropionamide stereoselectively, into S-(+)-2-phenylpropionic acid, making it possible that optically active 2-phenylpropionic acid and 2-phenylpropionamide be procured from racemic R, S-2-phenylpropionamide, or from racemic R,S-2-phenylpropionitrile via racemic R,S-2-phenylpropionamide.

Now, explanation will be given by the embodiment of the present invention. The micro-organisms used in the present invention are cultivated on the medium containing assimilable carbon sources, nitrogen sources and organic nutrients (glycerol, glucose, saccharose, fumaric acid, casamino acids, sodium glutamate, polypeptone, yeast extract, meat extract, etc.), inorganic salts essential for microbial growth (magnesium sulfate, iron chloride, potassium chloride, manganese sulfate, zinc sulfate, etc.), and crotonamide working as a inducer of the two enzymes or nitrile hydratase and amidase. Particularly, usage of fumaric acid and polypeptone is preferable because they allow a higher activity of amidase.

Cultivation should be performed at pH 6–8, at 15°–40° C. and for 1–5 days under aerobic conditions. Bacterial cells or treated bacterial cells (e.g., disrupted bacterial cells, crude or purified enzyme, immobilized bacterial cells or enzyme) are suspended in a aqueous solvent such as water or buffer. R, S-2-phenylpropionitrile or R, S-2-phenylpropionamide is added to the suspension and is hydrolyzed in the suspension.

Concentration of R, S-2-phenylpropionitride or R, S-2-phenylpropionamide in the suspension is typically 5–500 mM, preferably 10–100 mM and an amount of bacterial cells 0.01–10 weight % (dry weight) and pH of the suspension is adjusted to pH 5–9, preferably to pH 6–8. Suitable temperature of nitrilehydratase activity is at 0°–40° C., preferably at 25°–35° C., and suitable temperature of amidase activity is at 15°–50° C., preferably at 30°–45° C. These two enzymes, lose their activity at more than 40° C. and 50° C., respectively.

Further, according to the studies of the present inventors, nitrile hydratase activity is readily inhibited by the presence of S-(+)-2-phenylpropionic acid and ammonia which are produced as a result of amidase activity. It is preferable to set temperature which allows, at the initial phase of the reaction, R, S-2-phenylpropionamide to accumulate and nitrile hydratase activity to rise as high as possible as compared with amidase activity. Such temperature is in the range from 5° to 15° C.

When R, S-2-phenylpropionamide is used as a substrate, temperature should be set to raise amidase activity at a higher lever. Such temperature is in the range 15° to 30° C.

Crude S-(+)-2-phenylpropionic acid thus obtained is purified according to the known method. For example, bacterial cells are first removed by centrifugation and, if necessary, granules, proteins, polysaccharides are removed by ultrafiltration. Alternatively, crude S-(+)-2-phenylpropionic acid is treated with activated carbon, extracted with organic solvent in the presence of acid, and concentrated under vacuum. Remaining R-(−)-2-phenylpropionamide is purified according to the know method, isolated, and hydrolyzed with acid to give R-(−)-2-phenylpropionic acid.

SUMMARY OF THE INVENTION

The present invention provides a method of obtaining optically active 2-phenylpropionic acid and 2-phenylpropionamide such as S-(+)-2-phenylpropionic acid, R-(−)-2-phenylpropionamide, and R-(−)-2-phenylpropionic acid from R, S-2-phenylpropionitrile or R,S-2-phenylpropionamide using a bacterium belonging to Rhodococcus equi.

Optically active 2-phenylpropionic acid and 2-phenylpropionamide are recovered in high yield and in quantities according to the method of the invention.

PREFERRED EMBODIMENT

The preferred embodiment of the present invention will be described below, but the scope of the present invention shall not be limited by the embodiment. Analysis of nitrile, amide and acid during reaction processes was performed by HPLC.

EXAMPLE 1

(1) Preparation of bacterial cell suspension *Rhodococcus equi:*

TG328 was cultured in the medium described below at 25° C. for 72 hours. The bacterial cell was harvested, washed 50 mM phosphate buffer solution(pH 8.0), and resuspended in the same buffer (½ volume of the medium) to give bacterial cell suspension (35 mg/ml).

| Composition of the medium: | |
|---|---|
| Sodium glutamate | 2.0 g |
| Casamino acid | 5.0 g |
| Polypeptone | 2.0 g |
| Yeast extract | 2.0 g |
| Fumaric acid | 10.0 g |
| Potassium hydroxide | 10.0 g |
| Croton amide | 10.0 g |
| Potassium biphosphate | 5.0 g |
| Magnesium sulfate.7H$_2$O | 0.5 g |
| Iron dichloriden H$_2$O | 10 mg |
| Tap water | 1000 ml |
| pH | 7.0 |

(2) Asymmetric hydrolysis of R,S-2-phenylpropionitrile:

To 100 ml of the above suspension was added continuously R,S-2-phenylpropionitrile with care using a micro-test-tube pump so that the concentration of R,S-2-phenylpropionitrile in the solution did not exceed 50 mM, and the reaction was allowed to occur at 25° C. Two hours after starting the reaction, R,S-2-phenylpropionamide was rapidly produced and nitrile concentration gradually decreased. Three hours after starting the reaction, supply of nitrile was stopped, and the reaction was further continued for 4 hours. During the final 4 hours, the remaining nitrile was gradually consumed, and along with this consumption, about ½ amide produced was converted to S-(+)-2-phenylpropionic acid, resulting in production of 340 mM S-(+)-2-phenylpropionic acid and 360 mM R-(−)-2-phenylpropionamide.

EXAMPLE 2

To 100 ml of the bacterial suspension as utilized in Example 1, was added continuously R,S-2-phenylpropionitrile with caution so that the concentration R,S-2-phenylpropionitrile in the solution did not exceed 50 mM, and the reaction was allowed to occur at 10° C. for 30 hours. The nitrile supplied was instantly converted to amide so that precipitation of nitrile not undergoing reaction was scarcely observed. 660 mM S-(+)-2-phenylpropionic acid and 750 mM R-(−)-2-phenylpropionamide were obtained.

After removing bacterial cells by centrifugation, the reaction mixture was extracted with the organic solvent phase contained nitrile and amide. The aqueous phase, after being adjusted to pH 2.8, was extracted with chloroform, and the solvent was removed by evaporation, to give purified S-(+)-2-phenylpropionic acid.

The data collected for this product through IR analysis, NMR analysis and weight analysis were compared with these of the product commercially available, and it was confirmed that the product is S-(+)-2-phenylpropionic acid. Comparison of the data regarding the optical purity and optical rotatory power of S-(+)-2-phenylpropionic acid is given in Table 1.

TABLE 1

| | Optical purity (%) | Optical rotatory Power $[\alpha]_D^{20}$ |
|---|---|---|
| Example 2 | 99.4 | +64.9 |
| Standard | 93.8 | +70.5 |
| R-(-)-propionamide | — | −59.4 |

EXAMPLE 3

0.37 g of R-(−)-2-phenylpropionic amide obtained in the Example 2 was dissolved in 2 ml of concentrated HCl and reacted at 50° C. for 20 hours. The yield of 2-phenylpropionic acid was 70.0% and the R-(−)-isomer product was 97.9% e.e.

0.37 g of R-(−)-2-phenylpropionic amide was dissolved in 2 ml of concentrated HCl and was reacted in a sealed tube at 100° C. for 2 hours. The yield of 2-phenylpropionic acid was 98.0% and the R-(−)-isomer product was 92.4% e.e.

REFERENCE EXAMPLE 1

Rhodococcus sp. AK32 (FERM BP-1046) described in EP Publication No. 0348901 was grown in a culture medium described below at 28° C. for 24 hours. After growth, 10 ml of the culture [2% (v/v)] was added to each of four 2 liter kolbens, each kolben containing 500 ml of a culture medium described below, and the mixture was incubated with shaking at 28° C. for 60 hours.

| Culture medium | |
|---|---|
| Glucose | 1% |
| Yeast extract | 0.5% |
| Peptone | 0.5% |
| Potassium dihydrogenphosphate | 0.12% |
| Dipotassium hydrogen phosphate | 0.08% |
| Magnesium sulfate (MgSO$_4$.7H$_2$O) | 0.02% |
| Ferrous sulfate (FeSO$_4$.7H$_2$O) | 0.003% |
| Sodium chloride | 0.1% |
| Isobutylnitrile | 0.1% |

*The pH of a culture medium was adjusted to 7.2.

Bacterial cells were harvested by centrifugation and was washed once with an equal amount of 0.85% NaCl solution and with 100 mM phosphate buffer/pH7.4. The bacterial cells were then suspended in 100 ml of 100 mM phosphate buffer/pH7.4 to a final OD$_{610}$ 100. 0.4 ml of 60 mM R,S-2-phenylpropionitrile was added to 50 ml of the suspension at 10° C. and reaction was carried out with swirling. After 44 hours of reaction, 3.18 mM 2-phenylpropionic acid and 54.3 mM 2-phenylpropionicamide were obtained. 3N HCl was added to the reaction product to adjust pH 2.0 and the reaction product was then centrifuged to remove bacterial cells. After centrifugation, the supernatant was extracted with 50 ml of dichloromethane. The optical purity of 2-phenylpropionic acid was analysed as S-(−)-1-(naphthyl)ethylamide by high pressure liquid chromatography (HPLC) and the S-(+)-isomer product was 96.0% e.e.

What is claimed is:

1. A process for producing an optically active compound comprising:
   a) adding R,S-2-phenylpropionitrile to *Rhodococcus equi* TG328 having accession number FERM BP-3791 or enzymes derived therefrom, in order to convert the R,S-2-phenylpropionitrile to S-(+)-2-phenylpropionic acid and R-(−)-2-phenylpropionamide; and
   b) recovering S-(+)-2-phenylpropionic acid.

2. The process of claim 1, further comprising recovering said R-(−)-2-phenylpropionamide.

* * * * *